United States Patent
Vogt et al.

(10) Patent No.: US 10,059,479 B2
(45) Date of Patent: Aug. 28, 2018

(54) VACUUM CEMENTING SYSTEM

(71) Applicant: Heraeus Medical GmbH, Wehrheim (DE)

(72) Inventors: Sebastian Vogt, Erfurt (DE); Hubert Buechner, Nuremberg (DE); Tim Schnieber, Frankfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 349 days.

(21) Appl. No.: 14/923,970

(22) Filed: Oct. 27, 2015

(65) Prior Publication Data

US 2016/0045243 A1    Feb. 18, 2016

Related U.S. Application Data

(62) Division of application No. 13/808,452, filed as application No. PCT/EP2011/002867 on Jun. 10, 2011, now Pat. No. 9,272,803.

(30) Foreign Application Priority Data

Jul. 7, 2010   (DE) .......................... 10 2010 026 497

(51) Int. Cl.
*B65B 69/00* (2006.01)
*B01F 11/00* (2006.01)
(Continued)

(52) U.S. Cl.
CPC .......... *B65B 69/00* (2013.01); *A61B 17/8833* (2013.01); *B01F 11/0082* (2013.01);
(Continued)

(58) Field of Classification Search
CPC .... A61F 2002/30561; A61F 2002/4685; B01F 11/0082; B01F 13/0023; B01F 15/0206;
(Continued)

(56) References Cited

U.S. PATENT DOCUMENTS

| | | | |
|---|---|---|---|
| 4,671,263 | A | 6/1987 | Draenert |
| 4,973,168 | A | 11/1990 | Chan |

(Continued)

FOREIGN PATENT DOCUMENTS

| | | |
|---|---|---|
| CN | 1123132 A | 5/1996 |
| CN | 1163147 A | 10/1997 |

(Continued)

OTHER PUBLICATIONS

English translation of Decision of Rejection mailed in corresponding JP Application No. 2013-517058 dated Oct. 21, 2014.

(Continued)

*Primary Examiner* — Tony G Soohoo
(74) *Attorney, Agent, or Firm* — Norris McLaughlin & Marcus, P.A.

(57) ABSTRACT

A vacuum cementing system has at least one cement powder cartridge and a container-opening system. The container-opening system has at least one container for at least one liquid and/or at least one powder, an opening device, and an outlet opening for applying a negative pressure. When a negative pressure is being applied, the opening device is mobile relative to at least a part of the at least one container. The vacuum cementing system has a means for connecting the cement powder cartridge to the at least one container and utilizes necessary vacuum for automatically opening the at least one container.

4 Claims, 8 Drawing Sheets

Figure 1:
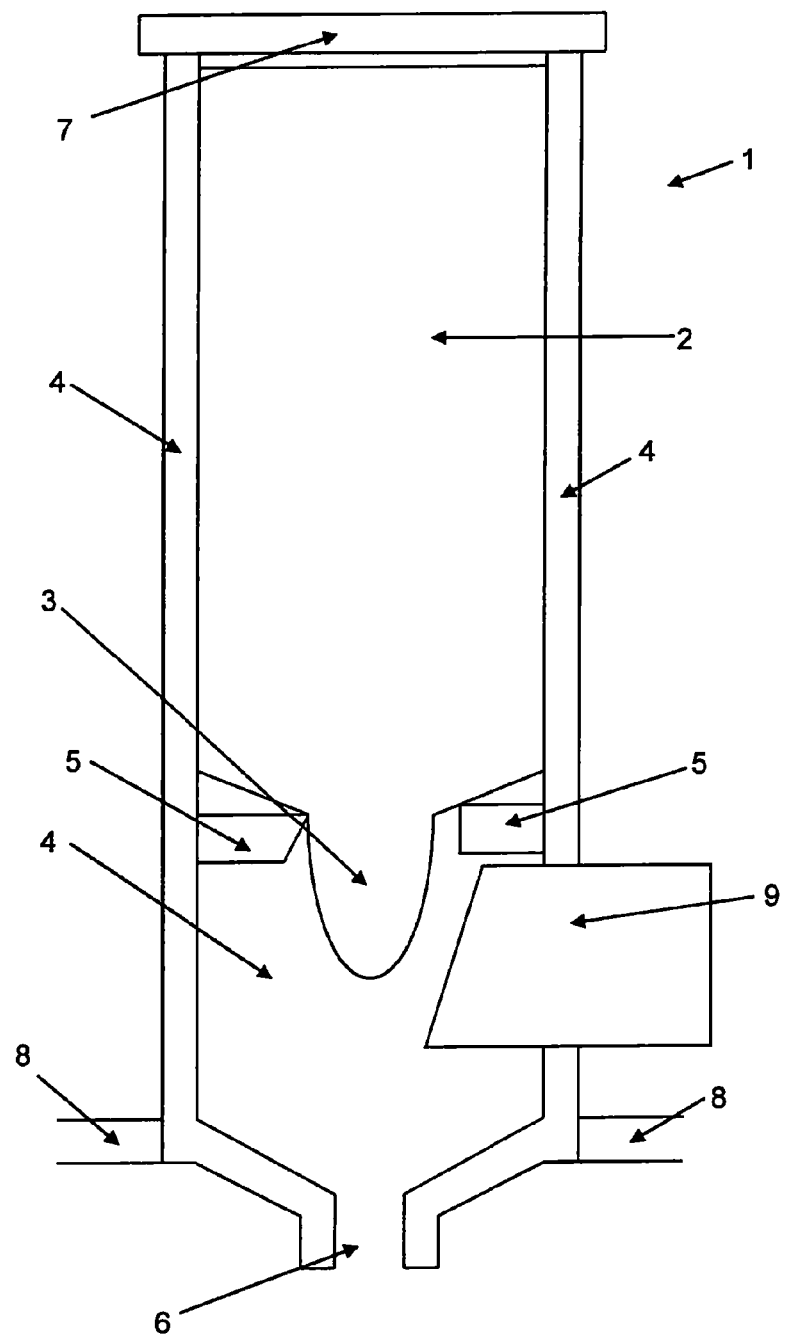

(51) Int. Cl.
- *B01F 13/00* (2006.01)
- *B01F 15/02* (2006.01)
- *A61B 17/88* (2006.01)
- *A61F 2/30* (2006.01)
- *A61F 2/46* (2006.01)

(52) U.S. Cl.
CPC ...... *B01F 13/0023* (2013.01); *B01F 15/0206* (2013.01); *B01F 15/0258* (2013.01); *B65B 69/0008* (2013.01); *A61F 2002/30561* (2013.01); *A61F 2002/4685* (2013.01)

(58) Field of Classification Search
CPC . B01F 15/0258; B65B 69/00; B65B 69/0008; A61B 17/8833
See application file for complete search history.

(56) References Cited

U.S. PATENT DOCUMENTS

| | | | |
|---|---|---|---|
| 5,100,241 | A | 3/1992 | Chan |
| 5,344,232 | A | 9/1994 | Nelson et al. |
| 5,551,778 | A | 9/1996 | Hauke et al. |
| 5,586,821 | A | 12/1996 | Bonitati et al. |
| 5,624,184 | A | 4/1997 | Chan |
| 5,997,544 | A | 12/1999 | Nies et al. |
| 6,312,149 | B1* | 11/2001 | Sjovall ............... B01F 11/0082 366/130 |
| 6,709,149 | B1* | 3/2004 | Tepic ............... A61L 24/06 366/139 |
| 7,073,936 | B1 | 7/2006 | Jonsson |
| 7,980,754 | B2 | 7/2011 | Wilander et al. |
| 8,128,276 | B2 | 3/2012 | Axelsson et al. |
| 2003/0155381 | A1 | 8/2003 | Chan |
| 2005/0105385 | A1* | 5/2005 | McGill ............... A61B 17/8805 366/139 |
| 2007/0016215 | A1 | 1/2007 | Wilander et al. |
| 2007/0034646 | A1* | 2/2007 | Higham ............... B65D 35/06 222/107 |
| 2008/0037362 | A1* | 2/2008 | Axelsson ............... B01F 13/06 366/139 |
| 2008/0037365 | A1* | 2/2008 | Axelsson ............... B01F 13/06 366/163.1 |
| 2014/0357753 | A1* | 12/2014 | Dolatkhani ............... A61L 27/16 523/116 |
| 2016/0051304 | A1* | 2/2016 | Vogt ............... A61B 17/8833 366/139 |
| 2016/0051305 | A1* | 2/2016 | Vogt ............... A61B 17/8833 366/98 |
| 2016/0354129 | A1* | 12/2016 | Vogt ............... A61B 17/8833 |
| 2017/0095283 | A1* | 4/2017 | Vogt ............... B01F 11/0054 |
| 2017/0156778 | A1* | 6/2017 | Vogt ............... A61B 17/8833 |
| 2017/0157578 | A1* | 6/2017 | Vogt ............... B01F 13/06 |
| 2017/0157579 | A1* | 6/2017 | Vogt ............... B01F 13/06 |

FOREIGN PATENT DOCUMENTS

| | | |
|---|---|---|
| DE | 3640279 A1 | 6/1987 |
| DE | 19532015 A1 | 3/1997 |
| EP | 0692229 A1 | 1/1996 |
| EP | 1005901 A2 | 6/2000 |
| EP | 1016452 A2 | 7/2000 |
| EP | 1020167 A2 | 7/2000 |
| EP | 1031333 A1 | 8/2000 |
| EP | 1741413 A1 | 1/2007 |
| JP | H0624735 U | 4/1994 |
| JP | 2007014771 A | 1/2007 |
| JP | 2008044372 A | 2/2008 |
| WO | 94/26403 A1 | 11/1994 |
| WO | 97/18031 A1 | 5/1997 |
| WO | 99/67015 A1 | 12/1999 |
| WO | 2010/012114 A1 | 2/2010 |

OTHER PUBLICATIONS

English translation of First Office Action mailed in corresponding Chinese Application No. 201180042874.8 dated Oct. 10, 2014.
Japanese Office Action for corresponding Japanese Application No. 2013 517058 dated Feb. 25, 2014.
Australian Office Action for corresponding Australian Application No. 2011276197 dated Dec. 10, 2013.
Breusch, S. J., et al., "Der Stand der Zementiertechnik bei Hueft-totalendorprothesen in Germany"; 1999, pp. 101-107; vol. 137, Z. Orthop.; Heidelberg, Germany.
Australian Search Report and Opinion for related Australian Application No. 2011276197 dated Apr. 9, 2013.
Charnley, John; "Anchorage of the Femoral Head Prosthesis to the Shaft of the Femur"; The Journal of Bone and Joint Surgery; Feb. 1960; pp. 28-30; Manchester, England.
International Search Report for related PCT Application No. PCT/EP2011/002867 dated Nov. 3, 2011.
International Preliminary Report on Patentability for related PCT Application No. PCT/EP2011/002867 dated Jan. 17, 2013.

* cited by examiner

VACUUM CEMENTING SYSTEM

This is a divisional patent application of U.S. Ser. No. 13/808,452, filed on Jan. 4, 2013, which is a 371 of PCT/EP2011/002867 filed 10 Jun. 2011 (international filing date), and claims the priority of German Application No. 10 2010 026 497.0 filed 7 Jul. 2010.

The invention relates to a vacuum cementing system comprising a container-opening system for opening containers.

The invention provides vacuum cementing systems for opening monomer ampoules for poly-methylmethacrylate bone cements (PMMA bone cements) prefilled with monomer liquid, as well as a device for storing and opening thereof that are made available to the medical user as full-prepack vacuum cementing systems.

PMMA bone cements have been known for decades and are based on the ground-breaking work of Sir Charnley (Charnley, J.: Anchorage of the femoral head prosthesis of the shaft of the femur. J. Bone Joint Surg. 42 (1960) 28-30.). The basic structure of PMMA bone cements has remained the same ever since. PMMA bone cements consist of a liquid monomer component and a powder component. The monomer component generally contains the monomer, methyl-methacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. Mixing the powder component and the monomer component, a dough that can be shaped plastically is generated by swelling of the polymers of the powder component in the methylmethacrylate. Mixing the powder component and the monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality (Breusch, S J et al.: Der Stand der Zementiertechnik in Deutschland. Z Orthop. 1999, 137: 101-07). Bone cements mixed in a vacuum have clearly reduced porosity and thus show improved mechanical properties. A large number of vacuum cementing systems has been disclosed of which the following shall be listed for exemplary purposes: U.S. Pat. Nos. 5,624,184, 4,671,263, 4,973,168, 5,100,241, WO 99/67015 A1, EP 1 020 167 A2, U.S. Pat. No. 5,586,821, EP 1 016 452 A2, DE 36 40 279 A1, WO 94/26403 A1, EP 0 692 229 A1, EP 1 005 901 A2, U.S. Pat. No. 5,344,232.

Vacuum cementing systems are used in the mixing of the PMMA bone cement in a vacuum in order to remove air inclusions from the cement dough. They are designed to produce a cement dough that is as homogeneous as possible and largely free of bubbles.

Cementing systems are a refinement, in which both the cement powder and the monomer liquid are already packaged in separate compartments of the mixing systems and are mixed with each other only right before application of the cement in the cementing system (U.S. Pat. No. 5,997,544, EP 0 692 229 A1, U.S. Pat. No. 6,709,149 B1). The issues of said systems include the transfer of the monomer liquid into the cement powder and the complete mixing of said two components in order to obtain a homogeneous cement dough that contains, in particular, no clusters of cement powder that has not been wetted by the monomer liquid. In the full-prepack mixing system, Optipac™ (Biomet Switzerland), which is currently commercially available in Europe, simple tubes, which are attached on the side in the lower part of the cartridge and puncture through the cartridge wall, are used to aspirate the monomer liquid approximately from aluminium composite pouches into the centre of the cement powder through the action of a vacuum. Aluminium composite pouches are manually moved against the tubes in order to open them, whereby the tubes puncture through the wall of the pouches.

Aluminium composite pouches have been known for packaging and storing monomer liquid for only a few years. Very good experience regarding the storage properties of monomer liquid has been made with glass ampoules. Glass ampoules have been in use for decades with good success with conventional polymethylmethacrylate bone cements. Another advantage of glass ampoules, aside from perfect sealing, is that they can be produced in large numbers at low prices. It is therefore reasonable to use glass ampoules for packaging and storage of monomer liquid in prepack vacuum cementing systems.

DE 195 32 015 A1 describes a device for mixing and dispensing multi-component products. This document proposes a device for the opening of ampoules that is based on a support socket about which an ampoule holder can rotate being provided on the outside of the cement cartridge. The head of the ampoule is situated on the inside of the support socket. Rotating the ampoule holder about the support socket, the ampoule head is sheared off the ampoule body. The liquid can then be transferred from the ampoule into the cartridge through an opening in the cartridge wall. WO 97/18031 A1 proposes a device, in which one ampoule is punctured on its bottom and the monomer liquid then can flow through the hollow mixing rod into the cement cartridge.

A system for the opening of ampoules in cementing systems is disclosed in EP 1 031 333 A1. In this system, a motion of the mixing rod against a wedge-shaped device in the cartridge head moves the ampoule head obliquely against the ampoule axis, whereby the ampoule head is sheared off the ampoule body. This is associated with a problem in terms of the relatively complex structure of the opening device and the danger of the wedge-shaped device getting lodged.

WO 2010/012114 A1 describes a device for the opening of ampoules. Analogous to DE 195 32 015 A1, this concerns a rotary mechanism for shearing off the head of the ampoule. The only difference from DE 195 32 015 A1 is that a rotary socket is moved against the ampoule holder rather than the ampoule holder being moved against the rotary socket as in DE 195 32 015 A1.

In summary, it can be concluded that all prepack vacuum cementing systems known to date contain monomer liquid containers that need to be opened manually. It would be more advantageous to have a forced automatic opening of the monomer liquid container proceed upon the application of vacuum on the cementing system. This would clearly simplify the handling of the vacuum cementing systems for the medical user and render them safer.

The invention is based on the object to a full-prepack vacuum cementing system, in which monomer liquid containers are opened automatically without manual action and thus the monomer transfer from a monomer container to a cement container can be triggered automatically.

Said object is met by a vacuum cementing system with at least one cement powder cartridge and a container-opening system, whereby the container-opening system comprises at least one container for at least one liquid and/or at least one powder, an opening device, and an outlet opening for applying a negative pressure, whereby when a negative pressure is being applied the opening device is mobile relative to at least a part of the container, and the vacuum cementing system comprises a means for connecting the cement powder cartridge to the container, and whereby the vacuum necessary for a cement dough with a low bubble content is additionally used for automatically opening the container.

It is of advantage if the container is arranged within a chamber and the outlet-opening is connected to the chamber.

In this context, it may be provided that the pressure difference moves an opening device as part of the container-opening system relative to at least one container, whereby the opening device is supported in the container-opening system like in a bearing such as to be mobile and/or the container is supported in the container-opening system like in a bearing such as to be mobile.

Moreover, the invention can provide a mobile plunger to be shifted in the container-opening system in such manner that the container or containers is or are opened through the motion of the plunger.

It is of advantage in this context if at least a part of the container is fractured, broken-off, cut open, cut off or pierced through the motion of the plunger such that the plunger acts as opening device.

Alternatively, it can be advantageous that the plunger takes up the container and that the motion of the plunger presses the container onto a part of the opening device, whereby the container is thus fractured, broken open, cut open or pierced.

The invention can provide a lever as opening device to be rotated or tilted through the motion of the plunger containing the container, and at least a part of the container to be broken off, cut open or pierced through the rotation of a lever arm of the lever.

Another alternative method according to the invention has the motion of the plunger tilting the container, whereby a part of the container becomes fixed in place in the container-opening system in suitable manner for the fixed part of the container to be broken off.

Another alternative results if at least a part of a wall of the container is moved relative to a mandrel that is attached to the container-opening system and acts as opening device and, as a result, cuts open or pierces and thus opens the wall of the container.

The invention can just as well provide that the container or containers contain a liquid, in particular a monomer liquid, and/or a powder, in particular a cement powder, whereby the content exits from the container after opening through the action of the negative pressure, in particular a vacuum, and is subsequently mixed with a powder, in particular a cement powder, or a liquid, in particular a monomer liquid, through the action of the negative pressure, in particular a vacuum.

In this context, the invention can provide the mixture to be pressed or made to leak from an applicator, preferably by means of an over-pressure.

The invention also relates to a container-opening system that is suitable for implementing a method of this type, comprising at least one container for at least one liquid and/or at least one powder, an opening device and an outlet opening for application of a negative pressure, whereby the opening device is mobile relative to at least one part of the container upon the application of a negative pressure.

In this context, the invention can provide the container and/or the opening device to be supported in the container-opening system like in a bearing such as to be mobile.

Moreover, the invention can provide the container-opening system to comprise a plunger that is supported like in a bearing such as to be mobile and, in particular, is cylindrical in shape.

In addition, it can be advantageous for the opening device to comprise the mobile plunger.

A refinement of the invention provides the mobile plunger to comprise a fork-shaped guidance for guiding a part of the container to be broken open and/or the interior of the plunger to be bevelled.

The invention can also provide the mobile plunger to be a hollow body that is closed on one side and has the container arranged in it.

In this context, it is advantageous for the opening device to comprise a lever that can be rotated within the container-opening system or to comprise a fin on the bottom of the hollow body that is closed on one side.

An alternative embodiment provides the container to comprise a preferably flexible wall and the opening device to be a mandrel or a blade, whereby the container is arranged in the container-opening system such as to be mobile and/or the wall can be deformed.

The invention can just as well provide for the container to comprise a liquid that contains a monomer component, preferably a polymerisable monomer such as, for example, methylmethacrylate, and an activator dissolved therein.

The object is also met by a vacuum cementing system comprising a container-opening system according to the invention, comprising at least one cement powder cartridge, whereby the container of the container-opening system preferably is an ampoule, in particular a monomer liquid container, and the vacuum cementing system comprises a means for connecting the cement powder cartridge to the ampoule.

In this context, the invention can provide the cement powder cartridge to comprise at least one mixing organ, in particular a feed plunger.

The invention can just as well provide a static mixer to be arranged at an application opening of the vacuum cementing system.

Moreover, the invention can provide the cement powder cartridge to contain a powder comprising one or more polymers, in particular based on methylmethacrylate and comonomers.

Direct opening of a container through the pressure difference shall be understood to mean that the external pressure moves a mobile means, for example a plunger, relative to the container and relative to the entire container-opening system and thus opens the container by mechanical means, i.e., for example, through breaking open, cutting open or piercing into a part of the container and/or of a container wall. For this purpose, the means for opening of the container is supported in the container-opening system like in a bearing such as to be mobile. The differential pressure therefore acts on the opening means resulting in a motion of the means.

Direct opening is evident if the pressure difference presses a container or a part of a container onto a static opening device. In this context, the differential pressure acts directly on the mobile container such that said container moves against the container-opening system. For this purpose, the container is supported in the container-opening system like in a bearing such as to be mobile. The container is then pushed or pressed onto an opening device that is connected to the container-opening system and opened mechanically by breaking open, cutting open or piercing into a part of the container and/or of a container wall.

Indirect opening is also evident if both the container and the opening device move, i.e. if both are supported in the container-opening system like in a bearing such as to be mobile.

The invention is based on the surprising finding that a vacuum in vacuum cementing systems can be put to use not only for removing air inclusions from the cement dough, but also for the opening of containers containing, for example, a monomer. Accordingly, the vacuum that is needed anyway in vacuum cementing systems for producing a cement dough with a low bubble content is, in addition, used for automatic opening of containers, for example monomer liquid containers. Generating a negative pressure in the cementing system, the pressure difference as compared to the surroundings thus generated is used to drive an automatic mechanical opening system. The negative pressure effects a relative motion of an opening device, such as, for example, a plunger, against the container, whereby a mechanical force is made to act on the container as a result of the relative motion. The action of said force opens the container and releases its content, for example a monomer required for the production of bone cement.

In the scope of the invention, the term, container, shall be understood to preferably mean glass ampoules, plastic ampoules, aluminium ampoules, and plastic composite pouches, including aluminium composite pouches.

Figure 2:
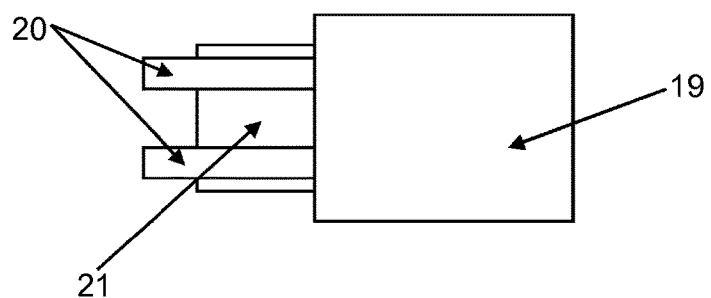
Figure 3:
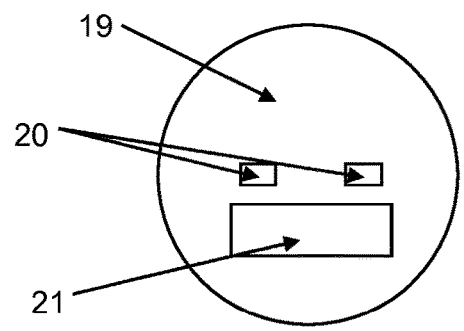
Figure 4:
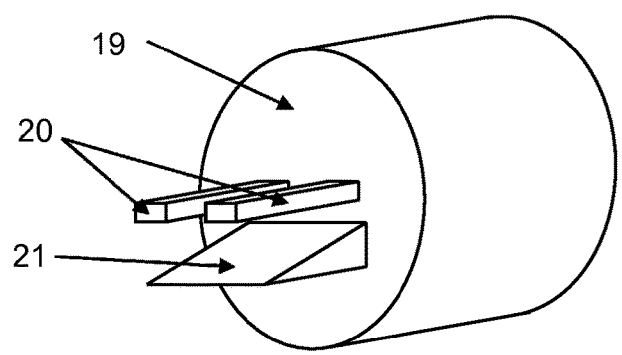
Figure 5:
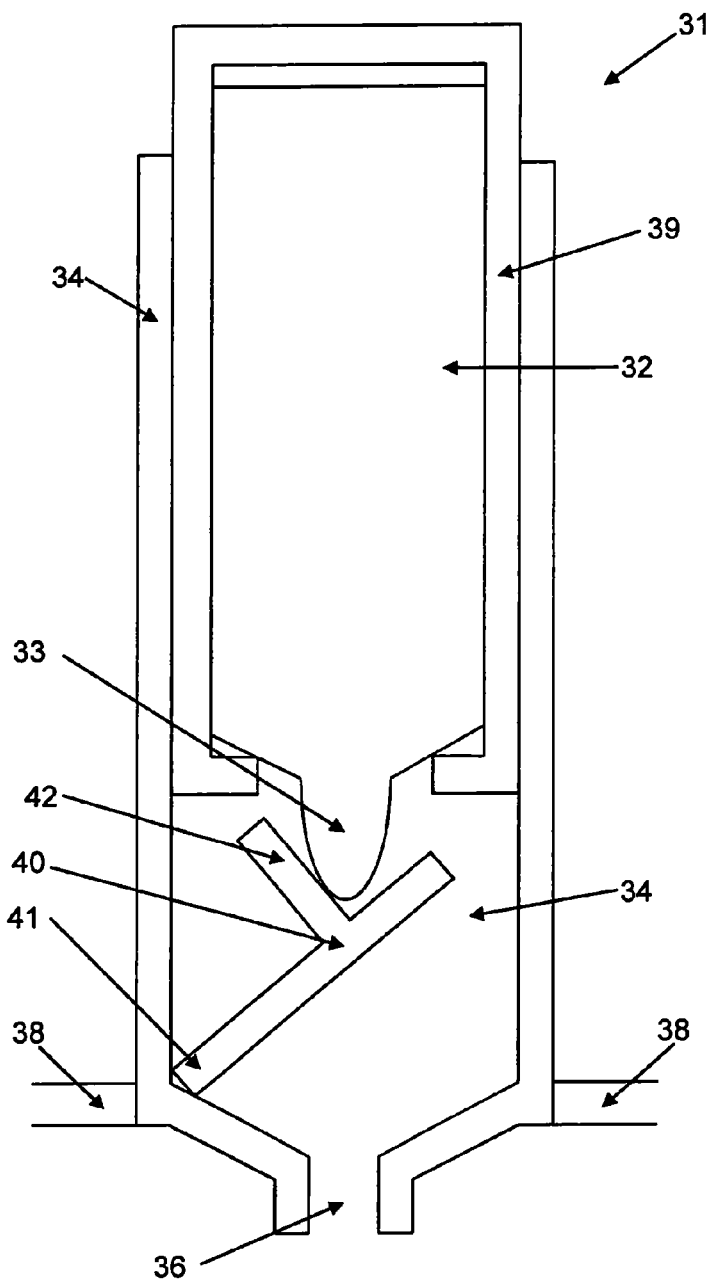
Figure 6:
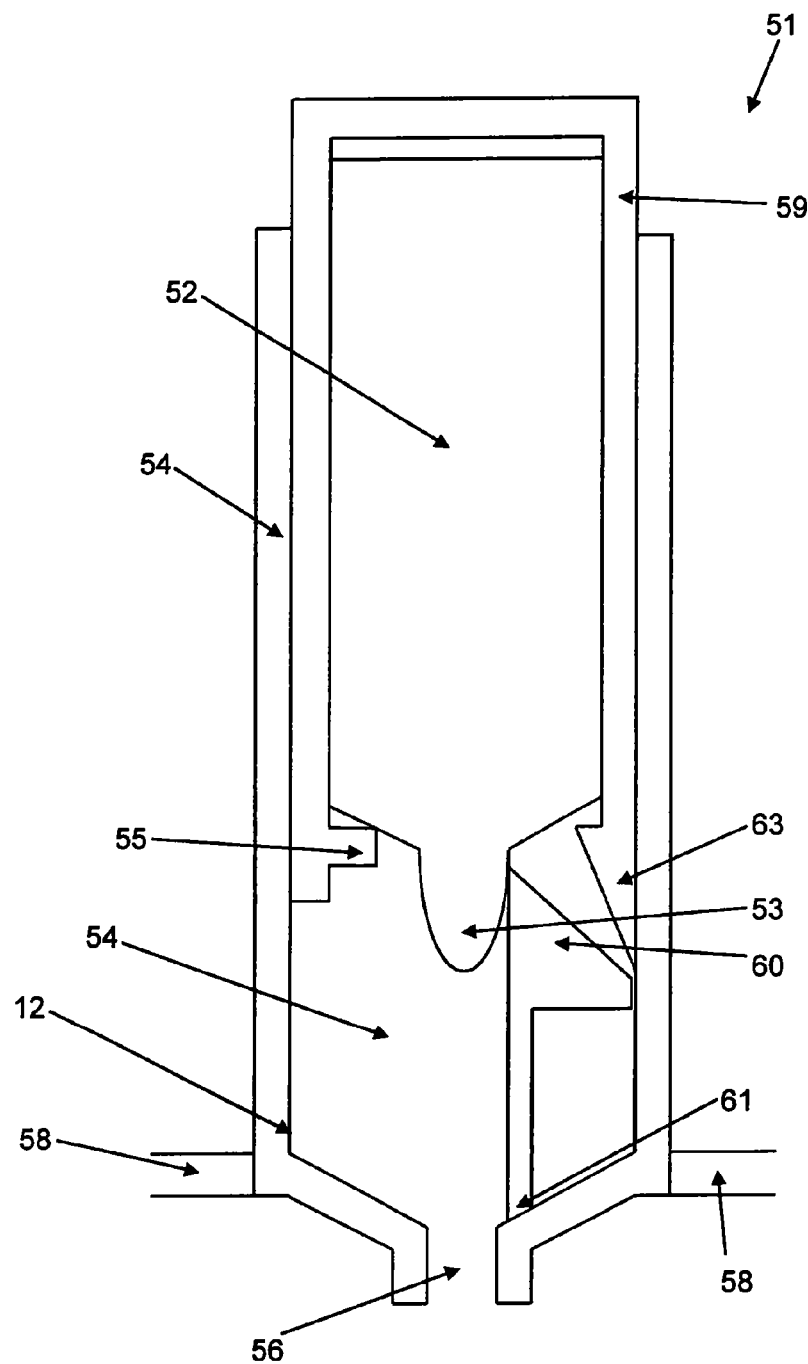
Figure 7:
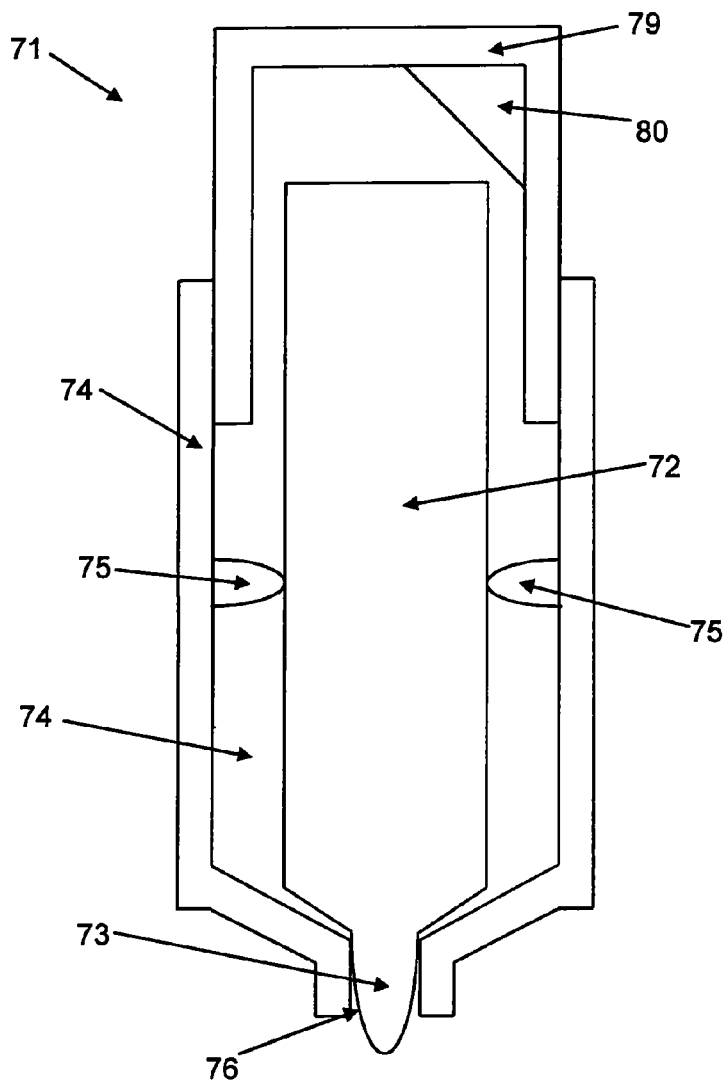
Figure 8:
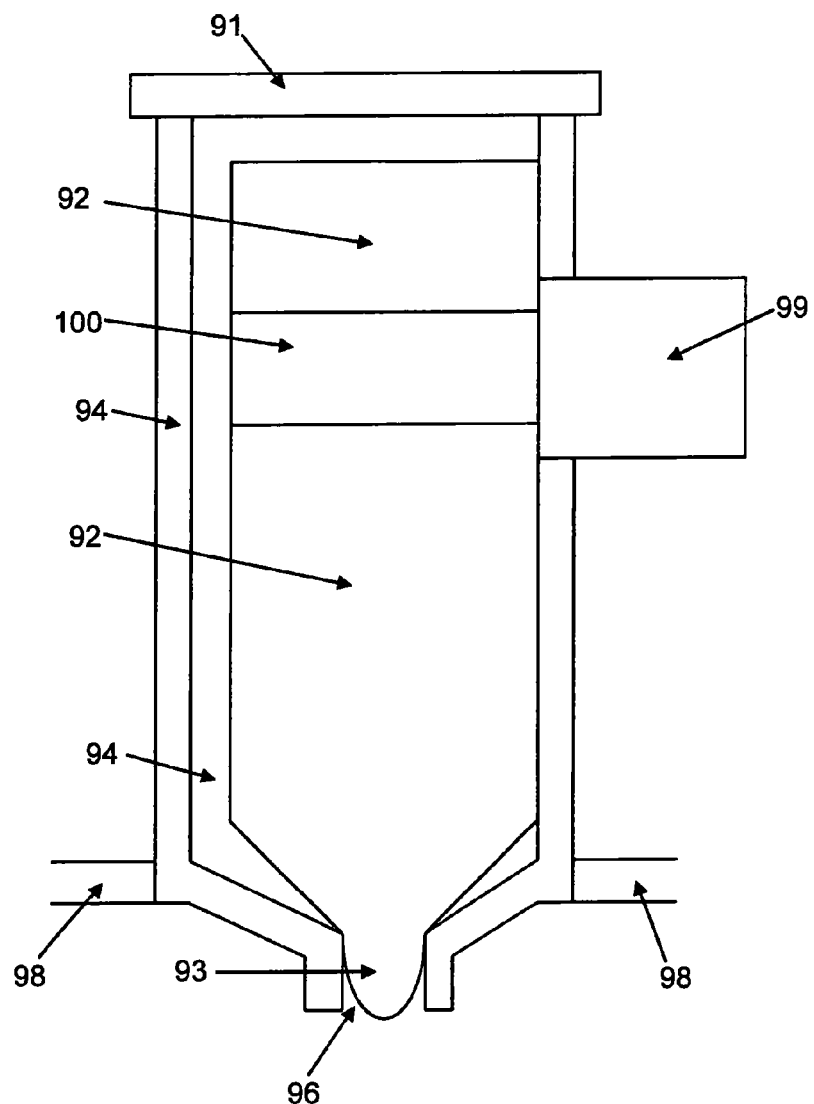
Figure 9:
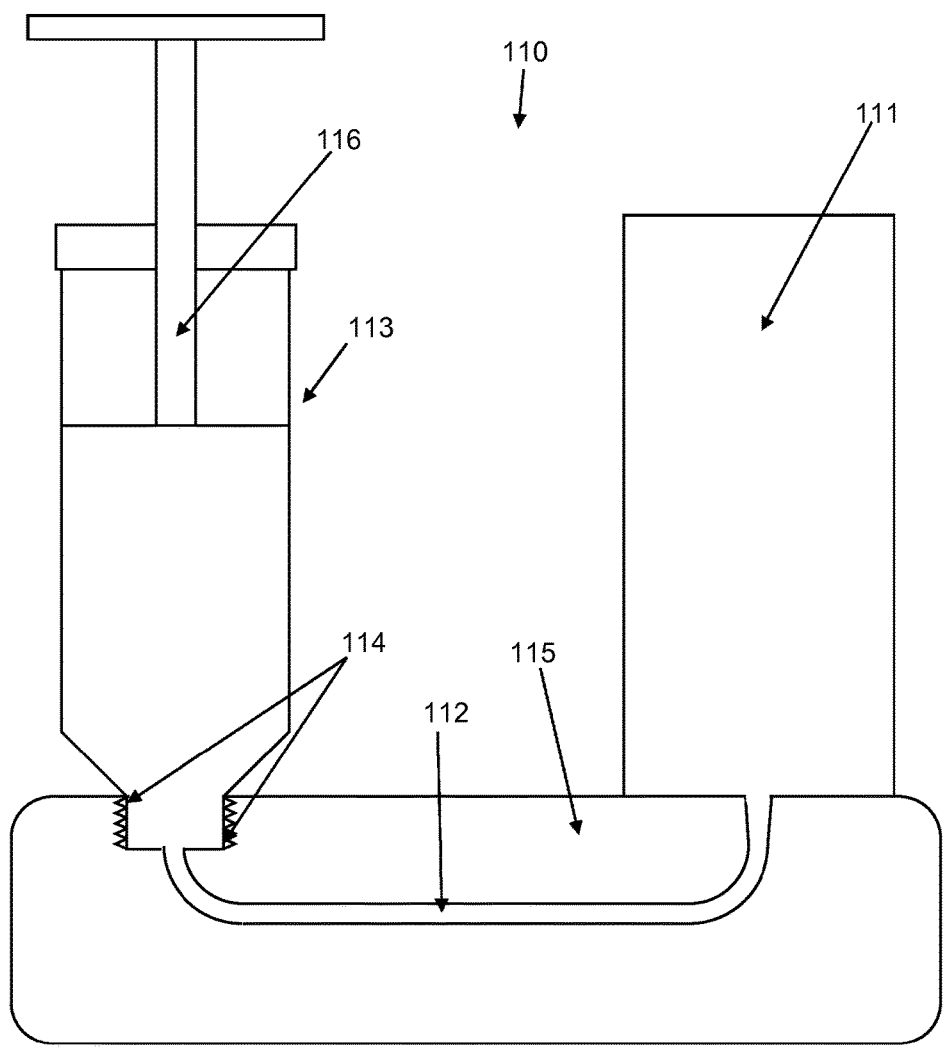
Figure 10:
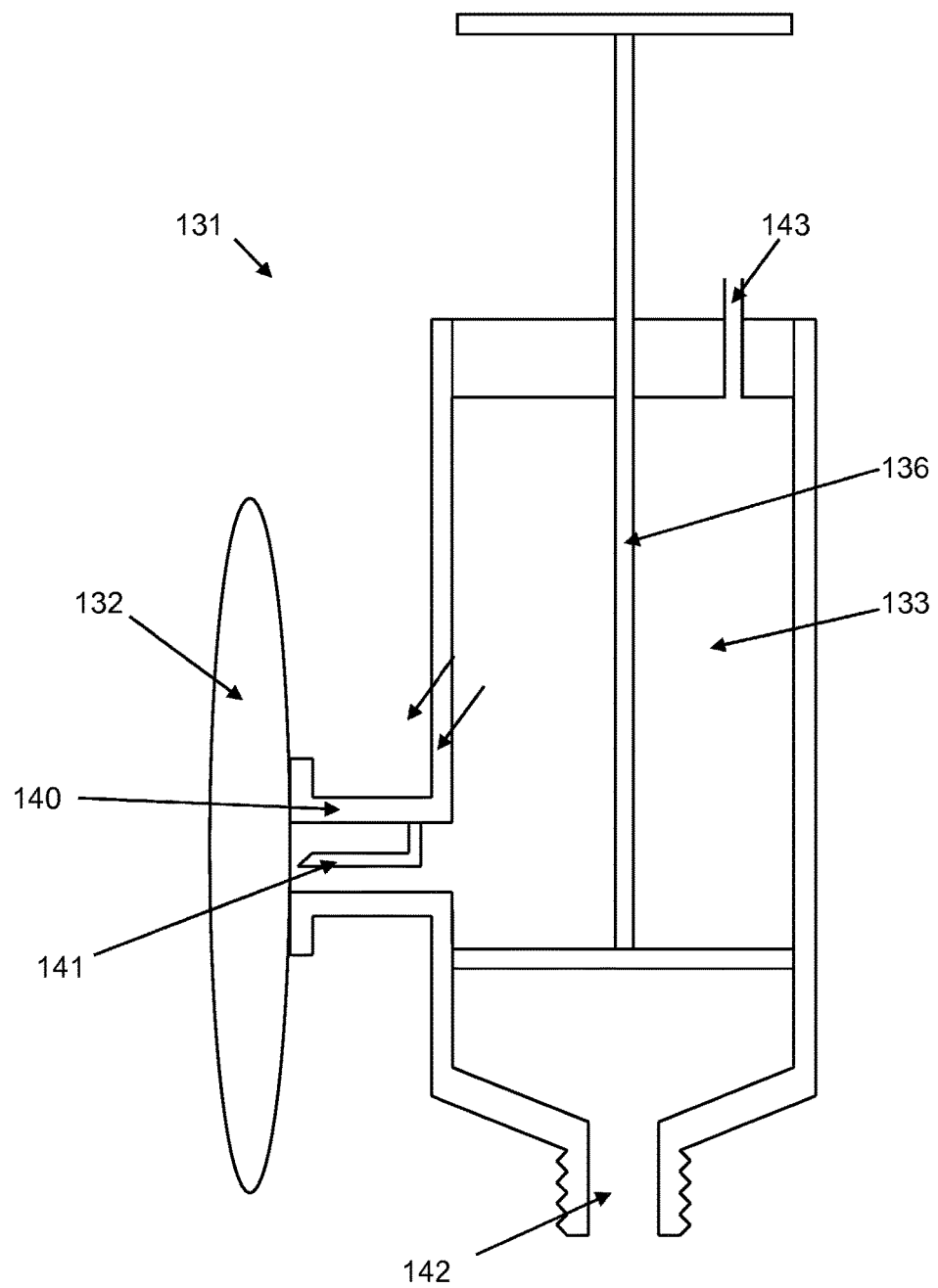

In the following, exemplary embodiments of the invention are illustrated through ten schematic drawings. In the figures:

FIG. 1: shows a schematic cross-sectional view in longitudinal direction of a container-opening system according to the invention with a closed container;

FIG. 2: shows a schematic top view onto a plunger having a fork-shaped guidance as opening device for a container-opening system according to the invention;

FIG. 3: shows a schematic front view of the plunger according to FIG. 2;

FIG. 4: shows a schematic perspective view of the plunger according to FIG. 2;

FIG. 5: shows a schematic cross-sectional view in longitudinal direction of an alternative container-opening system according to the invention with a closed container;

FIG. 6: shows a schematic cross-sectional view in longitudinal direction of a third container-opening system according to the invention with a closed container;

FIG. 7: shows a schematic cross-sectional view in longitudinal direction of a fourth container-opening system according to the invention with a closed container;

FIG. 8: shows a schematic cross-sectional view in longitudinal direction of a fifth container-opening system according to the invention with a closed container;

FIG. 9: shows a schematic cross-sectional view of a vacuum cementing system according to the invention; and FIG. 10: shows a schematic cross-sectional view in longitudinal direction of a sixth container-opening system according to the invention with a closed container.

Examples for vacuum cementing systems are illustrated in the following description of figures.

FIG. 1 shows a schematic cross-sectional view of a container-opening system (1) according to the invention that has a container (2) arranged in it in the form of an ampoule. The container (2) comprises a container head (3) and, according to FIG. 1, a container body situated above the head. A pre-determined breakage site is present between the container head (3) and the container body.

The container is arranged in a chamber (4) of the container-opening system (1) and is positioned by means of two connectors (5). An outlet opening (6) is provided in the chamber (4) below the container head (3). The upper side of the chamber (4) is closed through a lid (7). The lid (7) is connected to the chamber (4) by means of a thread or any other closure mechanism. The container-opening system (1) can be incorporated or integrated into another device that is shown here by means of the open walls (8).

A cylindrical opening is provided in the walls of the chamber (4) in the region of the container head (3) and has a cylindrical plunger (9) arranged in it that is mobile along its axis of symmetry. The side of the plunger (9) that extends into the inside of the chamber (4) is bevelled. The bevelling is to ensure that the container head (3) breaks off the container body easily when the plunger (9) is pushed into the inside of the chamber (4). The bevelling of the connector (5) situated opposite from the plunger (9) serves the same purpose. Both measures are intended to focus and enhance the force acting through the plunger (9) on the breakage zone.

The walls of the chamber (4) and the lid (7) are resistant to pressure, i.e. retain their shape even when a vacuum is generated on the inside of the chamber (4). The plunger (9) is lodged in a gas-tight press-fit in the opening of the walls of the chamber (4).

The method according to the invention can be implemented, for example, as follows: Firstly, a negative pressure is applied at the outlet opening (6). This establishes a negative pressure on the inside of the chamber (4) as well. The difference in pressure between the inside of the chamber (4) and the exterior surroundings of the chamber (4) causes a larger pressure, and therefore a larger force, to act on the surface of the plunger (9) facing outward than on the surface of the plunger (9) facing inward. The plunger (9) thus experiences a resultant force that drives it into the inside of the chamber (4). Once the static friction of the plunger (9), which is in a press-fit, is overcome through the resultant force, the plunger (9) moves to the inside of the chamber (4). Lastly, the plunger (9) is to hit against the container head (3) and shear it off. This opens the container (2). The content of the container (2) flows out of the container and through the outlet opening (6) to exit from the container-opening system (1).

Since modern vacuum cementing systems always generate a vacuum anyway, for example in order to mix a monomer liquid and a bone cement in a vacuum, said vacuum can concurrently be utilised to open the sterile closed container (2), in which the monomer liquid and/or the bone cement powder is/are situated. For example glass ampoules are suitable and customary containers (2) for the monomer liquid and/or the bone cement.

The static friction of the plunger (9) in the opening of the chamber (4) and/or the stability of the breakage zone of the container (2) or the cross-section of the plunger (9) can be adjusted in suitable manner in this context such that the container (2) and/or the glass ampoule is being opened only when the negative pressure in the chamber (4) is sufficient for a sufficiently bubble-free mixture to be generated from monomer liquid and bone cement.

The opening device in this exemplary embodiment is the plunger (9) that is supported like in a bearing such as to be mobile.

FIGS. 2, 3, and 4 show various views of schematic depictions of a plunger (19) with an alternative design for alternative container-opening systems according to the invention (not shown). The plunger (19) that is to function as opening device for containers comprises a fork-shaped guidance consisting of two fins (20) and further comprises a bevelled projecting plate (21). The fork-shaped guidance (20) is to define the motion of the plunger (19) relative to a container head. A suitable container for this purpose has a tapering between the container head and the container body that can be engaged by the fork-shaped guidance (20).

The plate (21) can be used to either break off and/or shear off the container head or the edges of the plate (21) are sufficiently sharp as to be capable of cutting through the walls of a container. The purpose of the fork-shaped guidance (20) and of the plate (21) is to render the process of opening more reproducible and more accurate. The intervening space between the two fins (20) can taper in the direction of the plunger (19) in order to allow for a container head to be severed when the plunger (19) moves. Then, there is no longer a need to have the plate (21) present.

FIG. 5 shows another schematic cross-sectional view of a second alternative container-opening system (31). The container-opening system (31) comprises a container (32) having a container head (33). The container (32) can contain, for example, a liquid. The container (32) is situated on the inside of a plunger (39) which in turn is lodged in mobile manner in a chamber (34). An outlet opening (36) is situated at the lower end of the chamber (34) below the container head (33). The entire container-opening system (31) is integrated into a device shown by means of open walls (38), such as, for example, a vacuum cementing system according to the invention.

The inside of the chamber (34) has a lever (40) situated in it that is supported like in a bearing such that it can be rotated and serves as opening device for the container (33) and has its first lever arm (41) supported at the walls of the chamber (34), whereby a second lever arm (42) loosely leans against the container head (33) in the form of a fin that branches perpendicularly off the first lever arm (41).

In a method according to the invention, a vacuum is generated in the chamber (34) by means of pumping the air out through the outlet opening (36). Due to the differential pressure between the inside of the chamber (34) and the surroundings of the container-opening system (31), the mobile plunger (39) containing the container (32) is pulled into the chamber (34). This concurrently leads to a rotation of the lever (40) through which a force is exerted on the container head (33) through the second lever arm (42). As soon as this force is sufficiently large, the container head (33) is fractured or broken off the container (32).

The liquid stored in the container (33) can then exit from the container (33) and flow out through the outlet opening (36) out of the container-opening system (31). Subsequently, the liquid can be guided to a cement powder through the negative pressure that is being applied to the outlet opening (36) and mixed with the cement powder in the vacuum cementing system (indicated by the open walls (38)).

FIG. 6 shows a schematic cross-sectional view of a third container-opening system (51) according to the invention. Like in the second exemplary embodiment, a container (52) is situated on the inside of a plunger (59) that is arranged in a gas-tight opening of a chamber (54) such as to be mobile. An outlet opening (56) is situated in the chamber (54) opposite from a container head (53) and can be used to apply a negative pressure to the chamber (54).

The plunger (59) comprises, on one side, a connector (55) for bracketing the container (52), and, on the other side, a wedge-shaped fin (63) having a bevelling on the side facing the container (52). A lever (60) that is provided in longitudinal direction with respect to the container (52) is situated in the chamber (54). The lever (60) is firmly connected to the walls of the chamber (54) in the region of the outlet opening (56) by means of a first lever arm (61) and comprises a bevelling on the side facing away from the container (52). The first lever arm (61) is made of an elastic, easily deformable material.

When a vacuum is applied to the chamber (54), the plunger (59) and the container (52) contained therein are pulled into the inside of the chamber (54). The bevelling of the wedge-shaped fin (63) slides between the walls of the chamber (54) and the bevelling of the lever (60). This pushes the lever (60) against the side of the container head (53) upon which the same breaks off the container (52). In addition, the tip of the lever (60) can puncture or cut into the pre-determined breakage site of the container (52) moving into the chamber (54).

Accordingly, the invention can provide the plunger (59) to possess a wedge-shaped fin (63) that is formed parallel to the ampoule axis, whereby a bevelling is provided on the side facing the ampoule side, and a lever (60) is situated in the chamber (54) that is formed in longitudinal direction with respect to the ampoule axis and has its upper lever end being situated adjacent to the ampoule head (53) such as to be freely mobile, whereby the lever (60) possesses a bevelling on the side facing away from the ampoule axis and the lever (60) is connected in mobile manner to the chamber (54) through the lower lever end (61).

Applying a vacuum, the fin (63) moves jointly with the plunger (59) in the direction of the ampoule head (53), whereby the bevelling of the fin (63) presses onto the bevelling of the lever (60). The lever (60) is fixed in place at its lower lever end (61) and its mobile upper lever end is forced to perform a rotary motion against the ampoule head (53). This causes the ampoule head (53) to break off the ampoule body. In this indirect opening of the container, the wedge (63) acts jointly with the lever (60) as opening device in the scope of the present invention.

FIG. 7 shows another schematic cross-sectional view of a container-opening system (71) according to the invention having a plunger (79) that is arranged in a chamber (74) such as to be mobile and is situated in an opening on the upper side of the chamber (74). The outer walls of the plunger (59) seal against the opening of the chamber (74) in gas-tight manner. A container (72) is positioned within the chamber (74) by means of connectors (75) at the walls of the chamber (74) and through an outlet opening (76) in the bottom of the chamber (74). A container head (73) of the container (72) is lodged in the outlet opening (76) and is connected to the container body by means of a pre-determined breakage site.

The connectors (75) essentially consist of a solid material and support the container (72) essentially only in spots. However, the provision of support along contact lines or surfaces is feasible as well. The contact sites of the connectors (75) define a centre of rotation about which the container (72) can be tilted.

The mobile plunger (59) is a hollow body having a closed end on one side. The internal cross-section of the plunger (79) is larger than the external cross-section of the container (72). A fin (80) in the form of a bevelling is situated on the inside of the plunger (79) and is arranged at the closed end and at a cylinder wall of the plunger (79). Regions of the container (72) project into the plunger (79).

The shape of the container head (73) and the shape of the outlet opening (76) are matched to each other such that they do not close with each other in form-fitting manner, i.e. the shape of the container head (73) does not perfectly match the shape of the outlet opening (76). This is to ensure that the outlet opening (76) does not become closed completely by the container head (73).

As a result, the atmosphere can be evacuated from the inside of the chamber (74) through the outlet opening (76) to establish a negative pressure in the chamber (74). The normal pressure in the surroundings of the container system (71) then pushes the plunger (79) in the direction of the outlet opening (76).

The fin (80) at the closed end of the plunger (79) is then pushed against an upper corner of the container (72) and the container (72) is tilted when the plunger (79) is pushed-in further. Since the container head (73) cannot follow the tilting motion of the container (72), it fractures or breaks off and the content of the container (72) is released through the outlet opening (76).

Accordingly, the fin (80) and the plunger (79) as well as the bracketing of the container head (76) jointly with the connectors (75) act as opening device in the scope of the present invention. Evidently, it is not that easy in this case to identify which parts form the opening device. Ultimately, a concerted action of different components is required in most cases to open the container. Said components then form the opening device in the scope of the present invention.

FIG. 8 shows another embodiment according to the invention of a container-opening system (91) for a method according to the invention. In this exemplary embodiment, the container (92) is again opened by breaking off or fracturing a container head (93) that is supported in an outlet opening (96) of a chamber (94). The chamber (94) is closed through a lid (97). The lid (97) seals the chamber (94) in gas-tight manner and in vacuum-tight manner.

The entire container-opening system (91) can be integrated into a vacuum cementing system (indicated through the open walls (98)).

An opening of the walls of the chamber (94) has a plunger (99) situated in it that is mobile in the opening and seals the opening in gas-tight manner. The plunger (99) is attached to the container (92) through a bracketing (100) in the form of a cuff.

In this case, the outlet opening (96) is not arranged in the centre of the chamber (94). As a result, the container (92) is situated tightly against the external walls of the chamber (94) on the side having the plunger (99), whereas there is still space to the walls of the chamber (94) on the opposite side.

What this attains is that the container (92) is rotated about an axis in the connection of the container head (92) to the container body when the plunger (99) penetrates into the chamber (94). Since the container head (91) cannot follow this motion, it is being broken off or fractured. This opens the container (92). The content of the container (92) can exit through the outlet opening (96) and is thus available to a vacuum cementing system that is connected to the container-opening system (91), to be mixed with another component.

According to the invention, the plunger is again moved due to a negative pressure being established in the chamber (94). For the outlet opening (96) to be useful, it is important that the container head (93) and the container (92) do not seal the outlet opening (96). Only this ensures that the outlet opening (96) can be used both for evacuating the chamber (94) and for discharging the content of the container (92).

Alternatively, a second free opening can be provided in the chamber (94) adjacent to the outlet opening (96) and allow the chamber (94) to be evacuated and the content of the container (92) to exit from the chamber (94). Rather than being supported in the outlet opening (96), it is feasible to simply provide a separate fastening for the container head (93) in the chamber (94) that is not connected to the region outside the chamber.

In this case, the opening device is formed by the plunger (99), the bracketing (100), and the bracketing of the container head (93), i.e. the outlet opening (96), and indirectly forces the container (92) to open.

FIG. 9 shows a vacuum cementing system (110) comprising a container-opening system (111) comprising a liquid-filled glass ampoule as container (not shown) that is connected to a cement powder cartridge (113) through a connecting means (112), for example a tubing. The cement powder cartridge (113) is connected to a foot part (115) of the vacuum cementing system (110) through a fastening means (114), such as, for example, a thread. The cement powder cartridge (113) comprises a feed plunger (116) that can be used to expel the content of the cartridge (113) from the vacuum cementing system (110) and/or to apply the ready-mixed cement.

A vacuum is used initially to open the glass ampoule in the container-opening system (111), as shown in the other figures. The vacuum aspirates the liquid from the container through the connecting means (112) into the cement powder cartridge (113) where it mixes with the cement. The mixture can be applied by means of the feed plunger (116). A static mixer (not shown) can be provided in the application opening (not shown) of the vacuum cementing system (110) to attain more thorough mixing of the liquid and the cement.

The method according to the invention and the vacuum cementing system (111) according to the invention are particularly advantageous and well-suited for PMMA bone cements, whereby a monomer component (for example containing methylmethacrylate and an activator) is used as liquid and a bone cement powder consisting of one or more polymers (for example based on methyl-methacrylate and comonomers) is used as powder component and/or these are contained in the container and the cement powder cartridge (113).

FIG. 10 shows another vacuum cementing system (130) comprising a container-opening system (131) that is somewhat different from the other exemplary embodiments. The container-opening system (131) comprises a container (132) in the form of a film pouch containing a liquid, and a tube (140), whereby a mandrel (141) having a blade is arranged on the inside of the tube (140). One wall of the film pouch (132) touches against the tube (140) in gas-tight manner. The mandrel (141) is attached to one of the tube walls. The tube (140) corresponds, to a limited extent, to the outlet openings (6, 36, 56, 76, 96) and the connecting means (112) in other exemplary embodiments.

A cement powder cartridge (133) is connected to the tube (140) on the side of the tube (140) that is opposite from the container (132). A feed plunger (136) is situated on the inside of the cement powder cartridge (133) and can be used to expel the content of the cement powder cartridge (133) from an application opening (142). A connector of the application opening (142) has a fastening means (134) attached to it in the form of a thread to which an applicator tip having a static mixer (not shown) can be connected. A vacuum connection (143) to which a vacuum pump and/or a source of negative pressure can be attached is arranged at the upper end of the cement powder cartridge (133).

In this embodiment of the method according to the invention, firstly, a negative pressure is applied to the vacuum connection (143). The film pouch (132) is pulled into the inside of the tube (140) and slit open through the blade of the mandrel (141). The content of the container (132) is aspirated into the tube (140). Simultaneously, the feed plunger (136) is pulled upwards. And lastly, the liquid can be passed from the container (132) through the tube (140) into the cement powder cartridge (133). In this location, it mixes with a cement powder that is contained in the cement powder cartridge (133).

Pressing by hand on the feed plunger (136) or applying a positive pressure to the vacuum connection (143), the feed plunger can subsequently be pushed in the direction of the application opening (142) as before. In the process, the mixture of cement powder/liquid is expelled from the application opening (142).

This embodiment according to FIG. 10 attains direct opening of the container (132). The container (132) itself moves by its flexible wall, which touches against the cross-section of the tube (140), onto the opening device, namely the mandrel (141), that is firmly connected to the container-opening system. It would also be conceivable that the container (132) has rigid container walls and is arranged in the tube (140) itself. For it to be aspirated onto the mandrel (141), it needs to seal against the walls of the tube (140) in gas-tight manner like the plunger (9, 39, 59, 79, 99) in the other exemplary embodiments.

The scope of the invention also includes the wall of the container (132) tearing autonomously in the region of the tube (140) due to the internal pressure of the container (132). A valve preventing reflux of the cement into the tube (140) and into the container (132) can be provided inside the tube (140).

Applicable to all exemplary embodiments, a sieve and/or a filter (not shown) can be arranged below the outlet opening (6, 36, 56, 76, 96) and/or in the tube (140), and can be used to retain fragments and/or residues of the container (2, 32, 52, 72, 92, 132) that may be produced when the container (2, 32, 52, 72, 92, 132) is cut open, cut off or fractured and/or when the container head (3, 33, 53, 73, 93) is being broken off.

Preferably, the container (2, 32, 52, 72, 92, 132) is an ampoule, in particular a glass ampoule.

A method according to the invention for the opening of ampoules in vacuum cementing systems can also be characterised in that a vacuum of an absolute pressure larger than or equal to 70 mbar acting on at least one plunger slides the plunger relative to one or more monomer liquid container(s), and in that the monomer liquid container(s) is or are thereby opened, whereby the opening proceeds through piercing and/or cutting open and/or breaking open.

The scope of the invention also includes devices comprising at least one cement powder cartridge (113, 133) having at least one mixing organ (116, 136), an ampoule (1, 31, 51, 71, 91, 111, 131) as monomer liquid container, a connecting means (112) for connecting the cement powder cartridge (113, 133), an ampoule container formed in at least one chamber (4, 34, 54, 74, 94) and at least one plunger (9, 19, 39, 59, 79, 99), whereby a) at least one plunger (9, 19, 39, 59, 79, 99) is arranged such that at least one chamber (4, 34, 54, 74, 94) is sealed from the external surroundings which are exposed to normal pressure;

b) the plunger (9, 19, 39, 59, 79, 99) is connected to the chamber (4, 34, 54, 74, 94) in gas-tight manner;

c) the cross-section of the chamber (4, 34, 54, 74, 94) is suitably adapted such that the plunger (9, 19, 39, 59, 79, 99) can be slid through the chamber (4, 34, 54, 74, 94) along the plunger axis;

d) the plunger (9, 19, 39, 59, 79, 99) is arranged such that it can be slid along the plunger axis;

e) the plunger (9, 19, 39, 59, 79, 99) can be connected by means of its side facing the chamber (4, 34, 54, 74, 94) to at least one site of the ampoule (2, 32, 52, 72, 92, 132) that is arranged in said chamber (4, 34, 54, 74, 94) in a non-positive fit-like or positive fit-like manner;

f) the chamber (4, 34, 54, 74, 94) contains at least one outlet opening (6, 36, 56, 76, 96) for fluids; and/or g) the plunger (9, 19, 39, 59, 79, 99) can be moved along its plunger axis through changes of the relationship between the pressure inside the chamber (4, 34, 54, 74, 94) and the ambient pressure and thus exerts a force on the ampoule (2, 32, 52, 72, 92, 132).

The invention can also provide the plunger (9, 19, 39, 59, 79, 99) to be arranged perpendicular to the ampoule axis and to be provided, at the plunger side facing in the direction of the inside of the chamber (4, 34, 54, 74, 94), to be perpendicular or oblique to the wall surface of the chamber (4, 34, 54, 74, 94), whereby the plunger side can have a smooth surface or a grooved surface. Exposed to a vacuum, the plunger (9, 19, 39, 59, 79, 99) moves in the direction of the ampoule head (3, 33, 53, 73, 93) and shears it off against the ampoule body.

The invention can also provide, if applicable, a fork-shaped guidance (20) to be attached on the inside of the plunger (9, 19, 39, 59, 79, 99), whereby the distance of the fins of the guidance (20) is equal to or larger than the diameter of the ampoule (2, 32, 52, 72, 92, 132) in the breakage zone. The guidance (20) can fix the ampoule (2, 32, 52, 72, 92, 132), between the ampoule head (3, 33, 53, 73, 93) and the ampoule shoulder, in place with respect to perpendicular motions along the ampoule axis. This ensures that the ampoule (2, 32, 52, 72, 92, 132) cannot get out of the way when the plunger (9, 19, 39, 59, 79, 99) is shifted onto the ampoule head (3, 33, 53, 73, 93). Fracturing of the ampoule (2, 32, 52, 72, 92, 132) is thus made more reliable.

The invention can just as well provide the plunger (9, 19, 39, 59, 79, 99) parallel to the ampoule axis in the form of a hollow cylinder (39, 59, 79) that is closed on one side and takes up the ampoule (2, 32, 52, 72, 92, 132) and can be shifted in the direction of the inside of the chamber (4, 34, 54, 74, 94) either jointly with the ampoule (2, 32, 52, 72, 92, 132) or separate from the ampoule (2, 32, 52, 72, 92, 132).

Just as well, a device according to the invention can be characterised in that the plunger (9, 19, 39, 59, 79, 99) can be shifted onto a first lever end of a lever (40) that is arranged in the chamber (4, 34, 54, 74, 94) and is arranged oblique to the ampoule axis below the ampoule head (3, 33, 53, 73, 93) and possesses at least one fin (42) perpendicular to the lever axis, whereby the fin (42) is oriented opposite from the ampoule head (3, 33, 53, 73, 93) and the first lever end of the lever (40) is situated freely in the chamber (4, 34, 54, 74, 94) and a second lever end (41) is connected to the chamber (4, 34, 54, 74, 94) such that it can rotate.

When the plunger (9, 19, 39, 59, 79, 99) is pushed onto the first lever end by applying a vacuum, the lever (40) performs a rotary motion, whereby the fin (42) is forced to also perform a rotary motion and thus a shearing motion against the ampoule head (3, 33, 53, 73, 93). This shears the ampoule head (3, 33, 53, 73, 93) off the ampoule body.

Another embodiment according to the invention is characterised in that the plunger (79) is provided as a hollow cylinder (79) that is closed on one side and possesses a fin (80) at the closed side of the cylinder, in that the fin (80) arranged in the direction of the open hollow cylinder (79) is bevelled, whereby the bevelling faces in the direction of the longitudinal axis of the plunger (79) and the largest slope of the bevelling is within the radius of the ampoule cross-section, and in that the ampoule (72) is arranged in the ampoule container (the chamber (74)) in such manner that the ampoule body has a sufficient distance from the internal wall of the ampoule container (74) such that the ampoule head (73) can be sheared off, i.e., for example, has a distance of more than 3 mm, whereby the ampoule head (73) is fixed in place in a non-elastic fastening hollow cylinder that has an internal diameter that is equal to or larger than the ampoule head (73).

The application of a vacuum moves the hollow cylinder (79) in the direction of the ampoule head (73). The fin (80) moves along in the direction of the ampoule head (73) concurrently. Due to its bevelling, the fin (80) presses the ampoule body perpendicularly with respect to the ampoule axis. The ampoule head (73) is fixed in place against twisting in a fastening hollow cylinder. This breaks the ampoule body off the ampoule head (73). Due to the lever effect, a minimal force acting on the end of the ampoule body opposite from the ampoule head (73) is sufficient to break the ampoule head (73) off the ampoule body.

The scope of the invention also includes a prepack vacuum cementing system, in which a foot part (115) has a cement powder cartridge (113, 133) having at least one mixing organ (116, 136) and a vacuum connection (143), an ampoule container (1, 31, 51, 91, 111, 131), a means (112, 140) for connecting the cement powder cartridge (113, 133) to the ampoule container (111), and at least one chamber (4, 34, 54, 74, 94) having a plunger (9, 19, 39, 59, 79, 99) arranged on it, whereby the plunger (9, 19, 39, 59, 79, 99) is provided as a hollow cylinder and takes up the ampoule (2, 32, 52, 72, 92, 132), whereby the plunger (9, 19, 39, 59, 79, 99) can be pushed onto a first lever end of a lever (40) that is arranged in the chamber (4, 34, 54, 74, 94) such as to be oblique to the ampoule axis and below the ampoule head (3, 33, 53, 73, 93) and which possesses at least one fin (42) perpendicular to the lever axis, whereby the fin (42) is oriented opposite from the ampoule head (3, 33, 53, 73, 93) and the first lever end of the lever (40) is situated freely in the chamber (4, 34, 54, 74, 94) and a second lever end (41) is connected to the chamber (4, 34, 54, 74, 94) such that it can be rotated.

The scope of the invention also includes a prepack vacuum cementing system comprising a foot part (115), a cement powder-filled cement powder cartridge (113, 133) having at least one mixing organ (116, 136), for example a feed plunger, and a vacuum connection (143), a monomer liquid-filled ampoule (2, 32, 52, 72, 92, 132), a means (112, 140) for connecting the cement powder cartridge (113, 133) to the ampoule container (1, 31, 51, 91, 111, 131), and at least one chamber (4, 34, 54, 74, 94) having a plunger (9, 19, 39, 59, 79, 99), whereby the plunger (9, 19, 39, 59, 79, 99) possesses a wedge-shaped fin (63) that is provided parallel to the ampoule axis, whereby a bevelling is arranged on the side facing the ampoule side, and a lever (60) that is provided in the longitudinal direction relative to the ampoule axis is situated in the chamber (4, 34, 54, 74, 94) and has a lever end that is situated freely mobile adjacent to the ampoule head (3, 33, 53, 73, 93), whereby the lever (60) possesses a bevelling on the side facing away from the ampoule axis, and in that the lever (60) is connected in mobile manner to the chamber (4, 34, 54, 74, 94) by means of the lower lever end (61).

A variant of the prepack vacuum cementing system is characterised in that a foot part (115) has a cement powder-filled cement powder cartridge (113, 133) having at least one mixing organ (116, 136) and a vacuum connection (143), a monomer liquid-filled ampoule (2, 32, 52, 72, 92, 132), a means (112, 140) for connecting the cement powder cartridge (113, 133) to the ampoule container (1, 31, 51, 91, 111, 131), and at least one chamber (4, 34, 54, 74, 94) having a plunger (9, 19, 39, 59, 79, 99) arranged on it, whereby the plunger (9, 19, 39, 59, 79, 99) is provided as a hollow cylinder that is closed on one side and possesses a fin (80) at the closed side of the cylinder, in that the fin (80) that is arranged in the direction of the open hollow cylinder is bevelled, whereby the bevelling faces in the direction of the longitudinal axis of the plunger (9, 19, 39, 59, 79, 99) and the largest slope of the bevelling is within the radius of the ampoule cross-section, in that the ampoule (2, 32, 52, 72, 92, 132) is arranged in the ampoule container (1, 31, 51, 91, 111, 131) in such manner that the ampoule body has a distance of more than 3 mm from the internal wall of the ampoule container (1, 31, 51, 91, 111, 131), and in that the ampoule head (3, 33, 53, 73, 93) is supported like in a bearing in a non-elastic hollow cylinder.

A design variant of the device is characterised in that the plunger (79) is arranged such that it can be pushed perpendicularly or approximately perpendicularly against the ampoule body, whereby the ampoule body is fixed in place to a plunger (99) through a fixation (100). The fixation (100) can be provided, for example, to be fork-shaped. One of the purposes of having the fixation (100) is to ensure optimal transmission of force from the plunger (99) to the ampoule body. Another purpose is that the fixation (100) stabilises the ampoule (92) during transport.

According to another embodiment, the prepack vacuum cementing system contains a foot part (115), a cement powder-filled cement powder cartridge (113, 133) having at least one mixing organ (116, 136) and a vacuum connection (143), a means (112, 140) for connecting the cement powder cartridge (113, 133) to the ampoule container (1, 31, 51, 91, 111, 131), one monomer liquid-filled ampoule (2, 32, 52, 72, 92, 132), and at least one chamber (4, 34, 54, 74, 94) having a plunger (9, 19, 39, 59, 79, 99), whereby the plunger (9, 19, 39, 59, 79, 99) is arranged such that it can be pushed perpendicularly or essentially perpendicularly in or above the ampoule container (1, 31, 51, 91, 111, 131), whereby the ampoule body is fixed in place to a plunger (99) by means of a bracketing (100).

The scope of the invention also includes a device comprising at least one cement powder cartridge (113, 133) having at least one mixing organ (116, 136), at least one film pouch (132) as monomer liquid container, at least one chamber (4, 34, 54, 74, 94), and at least one plunger (9, 19, 39, 59, 79, 99). Said device is characterised in that a tube (140) is provided, whereby a mandrel (141) having a tip or a mandrel (141) having a blade is arranged on the inside of the tube (140) and has its tip situated below the edge of the tube (140), and at least one external side of the film pouch (132) rests on the edge of the tube (140), and in that at least one vacuum connection (143) is present, whereby the vacuum connection is concurrently provided as opening for fluids.

Said device is based on the film pouch (132) touching against the edge of the tube (140) being pulled into the tube (140) upon the application of a vacuum. Its deformability and flexibility allow the film pouch to be pulled in. While it is being pulled into the tube (140), the film pouch (132) is pierced open or cut open by means of the mandrel (141) having the tip or the mandrel (141) having the blade such that the monomer liquid can flow through the tube (141) in the direction of the cement powder cartridge (133). It is advantageous for the edge of the tube (140) that has the film pouch (132) rest on it to be provided as a broad, flat edge. This allows the film pouch (132) to be glued directly onto the tube (140) using an adhesive or two-sided, ring-shaped adhesive tape. This can attain tight connection of the film pouch (132) to the edge of the tube (140).

The scope of the invention also includes a prepack vacuum cementing system that contains at least one cement powder-filled cement powder cartridge (133) having at least one mixing organ (136) and a vacuum connection (143), at least one monomer liquid-filled film pouch (132) and at least one plunger (9, 19, 39, 59, 79, 99), whereby the plunger (9, 19, 39, 59, 79, 99) is provided as a tube, whereby a mandrel (141) having a tip or a mandrel (141) having a blade is arranged on the inside of the tube (140) and has its tip situated below the edge of the tube (140), in that at least one external side of the film pouch (132) rests on the edge of the tube (140), and in that at least one vacuum connection is present, whereby the vacuum connection is concurrently provided as opening (6, 36, 56, 76, 96) for fluids.

The features of the invention disclosed in the preceding description and in the claims, figures, and exemplary embodiments, can be essential for the implementation of the various embodiments of the invention both alone and in any combination.

LIST OF REFERENCE NUMBERS 1, 31, 51, 71, 91, 111, 131 Container-opening system
2, 32, 52, 72, 92, 132 Container
3, 33, 53, 73, 93 Container head
4, 34, 54, 74, 94 Chamber
5, 55, 75 Connector
6, 36, 56, 76, 96 Outlet opening
7, 97 Lid
8, 38, 58, 98 Open walls
9, 19, 39, 59, 79, 99 Plunger
20 Fork-shaped guidance/fin
21 Bevelled plate
40, 60 Lever
41 First lever arm/centre of rotation
42 Second lever arm
61 Lever end/centre of rotation
63 Wedge-shaped fin
80 Fin/bevelling
100 Bracketing
110, 130 Vacuum cementing system
112 Connecting means
113, 133 Cement powder cartridge
114 Fastening means
115 Foot part
116, 136 Feed plunger
140 Tube
141 Mandrel
142 Application opening
143 Vacuum connection

The invention claimed is:

1. A vacuum cementing system comprising at least one cement powder cartridge and an container-opening system connected via a tube having an inside and a cross-section, wherein the at least one cement powder cartridge is provided at a first side of the tube, the vacuum cementing system comprising:
   a film pouch for at least one liquid and/or at least one powder provided at a second side of the tube opposite the first side of the tube and having a flexible wall, wherein the flexible wall contacts against the tube in a gas-tight manner;
   an opening device of the container-open system arranged on the inside of the tube, wherein the opening device comprises a mandrel or a blade attached to one wall of the tube; and
   an outlet opening for applying a negative pressure,
   wherein, when a negative pressure is being applied to the outlet opening, the film pouch, that is mobile with respect to the opening device, is pulled into the inside of the tube and opened by the opening device such that the film pouch itself moves, by the flexible wall contacting against the cross-section of the tube, onto the opening device, and
   further wherein, when the vacuum cementing system is located in the upright position, the film pouch, in its entirety, is offset with respect to a vertically extending plane defined by the at least one cement powder cartridge.

2. The vacuum cementing system according to claim 1, wherein the at least one cement powder cartridge comprises a feed plunger.

3. The vacuum cementing system according to claim 1, wherein the at least one cement powder cartridge comprises at least one mixing organ.

4. The vacuum cementing system according to claim 1 further comprising:
   an application opening provided at a first end of the at least one cement powder cartridge that is opposite with respect to the opening device provided at an opposite second end of the at least one cement powder cartridge.

* * * * *